United States Patent [19]

Aid et al.

[11] Patent Number: 4,827,430

[45] Date of Patent: May 2, 1989

[54] FLOW MEASUREMENT SYSTEM

[75] Inventors: James D. Aid; Norman F. Cameron, both of St. Petersburg; Thomas P. Hartranft, Safety Harbor, all of Fla.

[73] Assignee: Baxter International Inc., Deerfield, Ill.

[21] Appl. No.: 48,307

[22] Filed: May 11, 1987

[51] Int. Cl.[4] ................. G01F 15/075; G01P 5/20
[52] U.S. Cl. .................. 364/510; 364/413.07; 340/606; 73/195; 128/637
[58] Field of Search ......... 364/509, 510, 415, 416; 340/603, 606; 73/861.04, 195–197, 202, 203; 128/637, 638

[56] References Cited

U.S. PATENT DOCUMENTS

| | | | |
|---|---|---|---|
| 4,148,314 | 4/1979 | Yin | 364/416 |
| 4,206,504 | 6/1980 | Frey | 364/416 |
| 4,538,221 | 8/1985 | Crain et al. | 364/510 |
| 4,562,552 | 12/1985 | Miyaoka et al. | 364/510 |
| 4,569,012 | 2/1986 | Sekozawa et al. | 364/510 |
| 4,593,365 | 6/1986 | Haley, Jr. et al. | 364/510 |
| 4,708,021 | 11/1987 | Braun et al. | 364/510 |

*Primary Examiner*—Parshotam S. Lall
*Assistant Examiner*—Brian M. Mattson
*Attorney, Agent, or Firm*—Paul C. Flattery; Macdonald J. Wiggins; Charles R. Mattenson

[57] ABSTRACT

A flow rate measurement system and method suitable for monitoring filtrate flow in a hemodialysis apparatus, provides a pair of flow meters in series at the input of a dialyzer for producing electrical signals indicative of dialysate flow rate and a pair of flow meters in series at the output of the dialyzer for producing electrical signals indicative of dialysate plus filtrate flow rate. A computer receives the flow rate signals and is programmed to calibrate each flow meter during a calibration phase to correct for any variations in each pair to thereby produce corrective scale factors. During an operational phase of the apparatus, the program monitors the flow meters and provides an alarm if any changes between the readings of either of the pairs of flow meters occurs.

7 Claims, 2 Drawing Sheets

FLOW MEASUREMENT SYSTEM

BACKGROUND OF THE INVENTION

1. Field of the Invention

The present invention relates to flow measurement systems and more particularly to a flow measurement system for a hemodialysis apparatus having improved fault detection.

2. Description of the Prior Art

Hemodialysis equipment is utilized to remove excess fluids from a patient's blood. Such equipment utilizes a dialyzer having a path through which the blood from the patient flows in and out to be returned to the patient. The blood flow chamber includes a semipermeable membrane through which water and low molecular weight solutes can pass, but not blood. On the opposite side of the membrane, a dialysate chamber is provided through which a dialysate solution flows. The fluids passing through the membrane are picked up by the dialysate which flows out of the dialyzer. The removed fluids are known as filtrates.

To produce the flow of the filtrate through the membrane, there must be a greater pressure in the blood chamber than in the dialysate chamber. The difference in these pressures is referred to as the transmembrane pressure. The operator of the dialysis equipment controls the rate at which filtrate passes through the membrane by increasing or decreasing the transmembrane pressure. With many patients, hypotension and other complications resulting from poor fluid management are a major concern. In such instances, precise control of the volume and flow rate of the filtrate removed from the blood is very important.

To obtain closed control, it is known to use automatic filtration control systems. In such systems, the operator, before the treatment begins, presets the length of time for the treatment and the quantity of fluid to be removed during that time. The automatic controller then measures the elapsed time and the amount of fluid being removed during the process. At any time the fluid removal rate is too small to produce the quantity of fluid required during the remaining time, the controller calculates the rate of filtration needed to reach the fluid removal goal at the end of the treatment and compares that rate with the actual rate at such instant. If the actual rate is too high or too low, the controller will adjust the transmembrane pressure to achieve the rate required to meet the goal.

As will be understood, a controller depends upon having a very accurate measurement of flow of the filtrate through the membrane into the dialysate solution. This measurement can only be made by an accurate measure of the flow rate of dialysate into the dialyzer, an accurate measurement of the flow rate of dialysate plus filtrate out of the dialyzer, and a calculation of the increase in flow rate which would represent the filtrate added to the dialysate. The volume of dialysate passing through the dialyzer is typically greater than the volume of filtrate by a factor of ten or more. Thus, the measurement of volume flow of filtrate requires measurement of a small difference between two larger numbers. This imposes a severe accuracy requirement on the flow transducers.

In hemodialysis equipment manufactured by the assignee of the present application, a flow transducer is disposed at the dialysate input of the dialyzer and a second flow transducer is disposed at the dialysate output of the dialyzer which monitors the dialysate plus the filtrate. A highly accurate flow transducer of the bearingless type, manufactured by Precision Bearingless Flow Company, is used. This type of flow meter utilizes a ring rotor disposed in a vortex chamber having a plurality of symmetrically spaced jets circumferentially around the chamber. A fluid flowing through the jets causes the rotation of the rotor with a rate of rotation proportional to the rate of flow of fluid. The bearingless flow meter provides a plurality of reflective marks on the ring rotor which are monitored by an electrooptical sensor thereby producing an electrical signal whose frequency is proportional to the rate of rotation of the rotor. Once calibrated, these flow meters are specified by the manufacturer as having a 0.001% accuracy. In practice, before beginning treatment with the dialysis equipment, the dialyzer is bypassed, and a uniform flow is produced through the two transducers. The readings of the two flow transducers are compared, and a scale factor calculated to correct any difference in the readings of the two instruments.

Although the bearingless flow transducers satisfy the accuracy requirements, a problem can occur during the treatment of a patient. If the reading of either flow transducer should indicate a change not occasioned by an actual change in flow rates, the automatic filtration controller may accept the erroneous reading as a change in filtration and decrease the transmembrane pressure resulting in inaccuracies of the measurement. Such changes in operation of the bearingless flow transducer have been observed which appear to be caused by slight imbalances in the ring rotors causing an occasional wobble mode of rotation causing the indicated flow rate drops. Therefore, there is a need for a flow rate measurement system which will include means for determining faulty readings of either input or output flow transducers.

SUMMARY OF THE INVENTION

The present invention is a flow measurement system having a controller which will automatically determine when any change in readings from the flow meters occurs and will automatically determined whether such changes are due to a faulty flow measuring device. The system makes use of redundancy in combination with a computer controller. Two bearingless flow meters are installed in series at the dialysis input of the dialyzer. A bypass valve is connected between the flow meters and the dialyzer. Two bearingless flow meters are similarly connected in tandem at the dialyzer dialysate output in series with a calibration valve. The bypass valve in the input serves to stop the flow of dialysate into the dialyzer and bypasses it to the input of the second output flow transducer. The calibration valve, as discussed below, may be closed by the computer to bypass the dialyzer. The two input flow transducers measure the in-flow of the dialysate while the two output flow transducers measure the out-flow of the dialysate plus filtrate.

Each sensor generates an electrical signal which is in the form of a train of pulses at a frequency depending upon the rotational rate of the rotors in the flow transducers. For example, a 500 ml per minute flow rate may produce a nominal output frequency of 220 Hz. The signal from each of the four flow transducers is connected to a digital computer. During an initial calibration of the system, the dialyzer connections are manually bypassed. A fixed flow of dialysate is provided through the four flow transducers in series. Typically, a flow of 500 ml per minute is used. The computer averages the frequency rate of each signal from the four flow transducers. Since the flow is the same through each transducer, the computer notes any differences in the average frequency among the four flow transducers and calculates calibration scale factors as required to compensate for any slight difference that may occur due to manufacturing tolerances or the like. During the calibration procedure, it is required that the frequency difference among the four flow transducers not exceed a preselected value, for example, 20 Hz. If this occurs, an indication of a fault will be shown on a display associated with the computer.

The calibration tests involve a first phase of taking samples of measurements of all four transducers at the same time for a constant flow rate. A preselected number of samples is taken, and, after all the samples have been gathered, the average and the standard deviation for each of the transducers is calculated. If the standard deviation for any of the sensors is greater than 10% of the respective average or if any of the frequencies measured exceed twice the respective standard deviation, a fault may be indicated.

Once all of the tests are passed, the scale factors are calculated to account for the differences between the flow sensors.

After calibration is complete and an operation of the hemodialysis equipment is begun, the computer will monitor the output from each of the flow transducers, applying the scale factors as determined during calibration. The computer also monitors the corrected flow measurements of the two input transducers and the two output transducers. If a difference between the two input transducer measurements or the two output transducer measurements is noted by the computer, an automatic check is run to determine if the flow transducers are within tolerance. If the detected error continues, or is indicated to be beyond acceptable limits during the automatic calibration recheck, a fault is noted, the procedure halted and the problem corrected. In some instances, cleaning of the flow transducer in error will correct the problem. Advantageously, the original calibration of the flow transducers may be verified during a treatment on the apparatus.

It is therefore a principal object of the invention to provide a system for flow rate measurement of a dialysate and dialysate plus filtrate utilized in hemodialysis equipment having redundancy and automatic verification of the calibration and the flow meter readings.

It is another object of the invention to provide a flow rate measuring system in hemodialysis equipment which will automatically recognize a fault in the flow measurement during operation of the equipment and provide an alarm to the operator.

It is still another object of the invention to provide a filtrate flow measurement system in a hemodialysis equipment having a first pair of bearingless flow transducers at dialysate input to the dialyzer, and a second pair of bearingless flow transducers in series at the dialysate plus filtrate output.

It is yet another object of the invention to provide a system for flow rate measurements having redundancy and automatic calibration, verification and fault indication during use of the system.

These and other objects and advantages of the invention will become apparent from the following detailed description when read in conjunction with the drawings.

DETAILED DESCRIPTION OF THE PREFERRED EMBODIMENT

Figure 1:
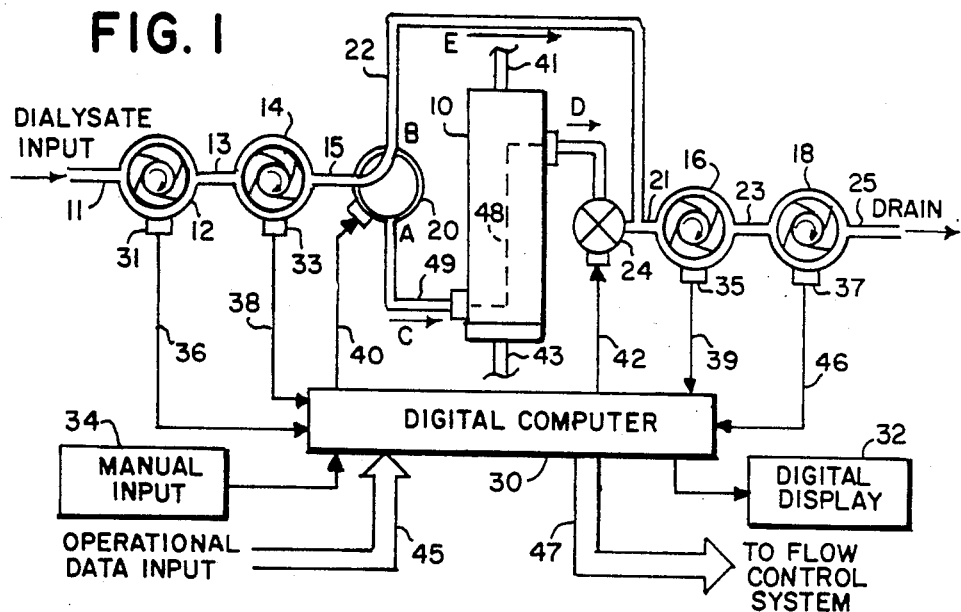
FIG. 1 is a simplified schematic diagram of the dialyzer portion of a hemodialysis apparatus utilizing the flow rate measurement systems of the invention.

Referring to FIG. 1, a schematic of a dialyzer 10 is shown having an input 41 into which the patient's blood flows with an outlet 43 from which the blood less the extracted fluids flows. A dialysate path 48 through dialyzer 10 is indicated by the dashed line. Fresh dialysate is input via line 11 to a pair of bearingless flow meter transducers or sensors 12 and 14 connected in tandem by line 13 such that the rate of flow through each is the same. Flow transducers 12 and 14 have electrooptical rotor speed pickoffs 31 and 33, respectively, which will each produce an ac signal whose frequency is directly proportional to the rate of rotation of the respective rotors. Output line 15 from the second input flow transducer 14 connects to an electrically operated bypass valve 20 shown schematically in the bypass position. As will be recognized, valve 20 may connect input line 15 to bypass line 22 via port B or to dialyzer input line 49 via port A and is controlled by a signal on lead 40. When valve 20 is in the operate mode, the dialysate will flow via line 49 through the dialysate path 48 of dialyzer 10 to electrically controlled calibration valve 24 as indicated by arrows C and D. At such time, calibration valve 24 will be open such that the dialysate plus filtrate indicated by arrow D will flow via line 21 to flow transducer 17.

However, in a calibration check condition shown in FIG. 1, the dialysate into line 11 will bypass dialyzer 10 and will flow via line 22 as indicated by arrow E to flow transducer 16. In such condition, calibration valve 24 is closed by a signal on lead 42 preventing any back flow into dialyzer 10. A pair of output bearingless flow transducers 16 and 18 is connected to line 21 and in tandem by line 23. Output line 25 from the second output flow transducer 18 connects to a drain for disposal of the dialysate plus filtrate from the patient's blood. Flow transducers 16 and 18 are identical to input flow transducers 12 and 14 and nominally have the same characteristics. AC signals will appear on lines 39 and 46 proportional to the rates of rotation of the rotors of flow transducers 16 and 18 from electrooptical pickoffs 35 and 37, respectively.

The operation of the flow measurement system is controlled by digital computer 30. Digital computer 30 is programmed to perform a number of functions in the operation of a hemodialysis apparatus incorporating the invention. Of particular interest here, computer 30 is programmed to calibrate the flow measurement system prior to the treatment of a patient. In one hemodialysis equipment, the operator disconnects dialyzer 10 and connects line 15 directly to line 21. Upon a manual input from manual input device 34, the computer initiates a calibration sequence. Signals on bus 47 to the flow control system energizes the dialysate pump producing a preselected fixed rate of flow of dialysate solution at input 11. As will be recognized, the output through drain line 25 will be exactly equal to the flow rate input at 11 since the four transducers 12, 14, 16, and 18 are in series.

As the dialysate solution passes through each of the flow tranducers, the rotor thereof will spin at a rate determined by the rate of flow of dialysate. A photoelectric pickup in electrooptical pickoff system 31 of transducer 12 will produce an ac signal on lead 36 directly proportional to the speed of rotation of the rotor of flow transducer 12. Similar ac signals will be produced by transducers 14, 16 and 18. Ideally, each of the four transducers should produce exactly the same frequency signal for the same flow rate. However, due to unavoidable manufacturing variations, it is expected that these frequencies will vary slightly from one transducer to another. Computer 30 will correct this variation by calculating appropriate scale factors.

Briefly, computer 30 samples the outputs from all four flow transducers to obtain a plurality of samples over a preselected period of time. These samples are analyzed by an appropriate software program to determine if the differences in frequency among the tranducers are within expected tolerances, and if so, the program proceeds to calculate scale factors to apply to each flow meter to bring all of the readings into coincidence. These scale factors are then stored in temporary memory for use during the following treatment of a patient. If the initial samples and calibration procedures indicate an out-of-tolerance flow meter, a fault is indicated on digital display 32 alerting the operator to determine the problem. If the problem is caused by contaminants in the indicated flow meter, it may be corrected by appropriate cleaning or replacement of filters and the like. After calibration is complete, the computer 30 will control bypass valve 30 to connect line 15 to input line 49 of dialyzer 10 and will operate calibration valve 24 to open the dialysate output from the dialyzer 10. Digital display 32 will indicate to the operator that the system is calibrated and in condition to begin treatment of the patient.

After the initial calibration phase, the operator reconnects the dialyzer into the system. At this point, the computer may institute a test and update phase. In such case, a control signal on line 40 will switch bypass valve 20 to the position shown in FIG. 1 and a signal on line 42 will close calibration valve 24. Thus, the dialyzer 10 is bypassed by line 22. The computer records a number of samples from the four flowmeters, applies the previously calibrated scale factors, and calculates an average rate for each flowmeter. An average system flow rate is determined and compared to each individual flowmeter average flow rate. If the differences in the values are within a preselected tolerance of the system average, calibration is complete and treatment of the patient is started. If the test and update procedure fails after several times, a major fault is indicated.

During a treatment, digital computer 30 continues to monitor the outputs from input flow transducers 12 and 14 and to compare their readings which should be identical when the scale factors are applied. Similarly, computer 30 monitors output flow transducers 16 and 18 for equal flow rate indications. If any deviation is noticed during treatment, digital computer 30 initiates the test and update phase to recheck calibration and, if necessary, modifies the scale factors if the readings are otherwise within tolerance. If a fault is indicated in any of the flow meters, a fault alarm may be displayed on digital display 32 along with an appropriate audible alarm to alert the operator.

Computer 30 also serves to control the rate of extraction of filtrate from the patient's blood in accordance with inputs from manual input 34 introduced by the operator prior to treatment. For example, the total time of treatment is preset and the volume of filtrate to be removed is also preset. The computer then monitors the rate of filtrate extraction from the patient's blood by subtracting the reading from input flow transducers 12 and 14 from the reading of output flow transducer 16 and 18. The computer continually calculates the total removed filtrate and the rate of removal. It continually compares this rate to the required rate and calculates whether, in the remaining time of treatment, the required volume of filtrate will be reached. If the calculations indicate an excessive extraction rate or an insufficient extraction rate, the computer will control the transmembrane pressure to correct the flow of filtrate such that the proper amount will be removed from the blood in the remaining time of treatment.

Bus 45 provides other system operational data to computer 30. For example, a signal from a start switch is required for the system to begin a treatment. Similarly, the blood pump must be active during operation of the dialyzer.

Figure 2:
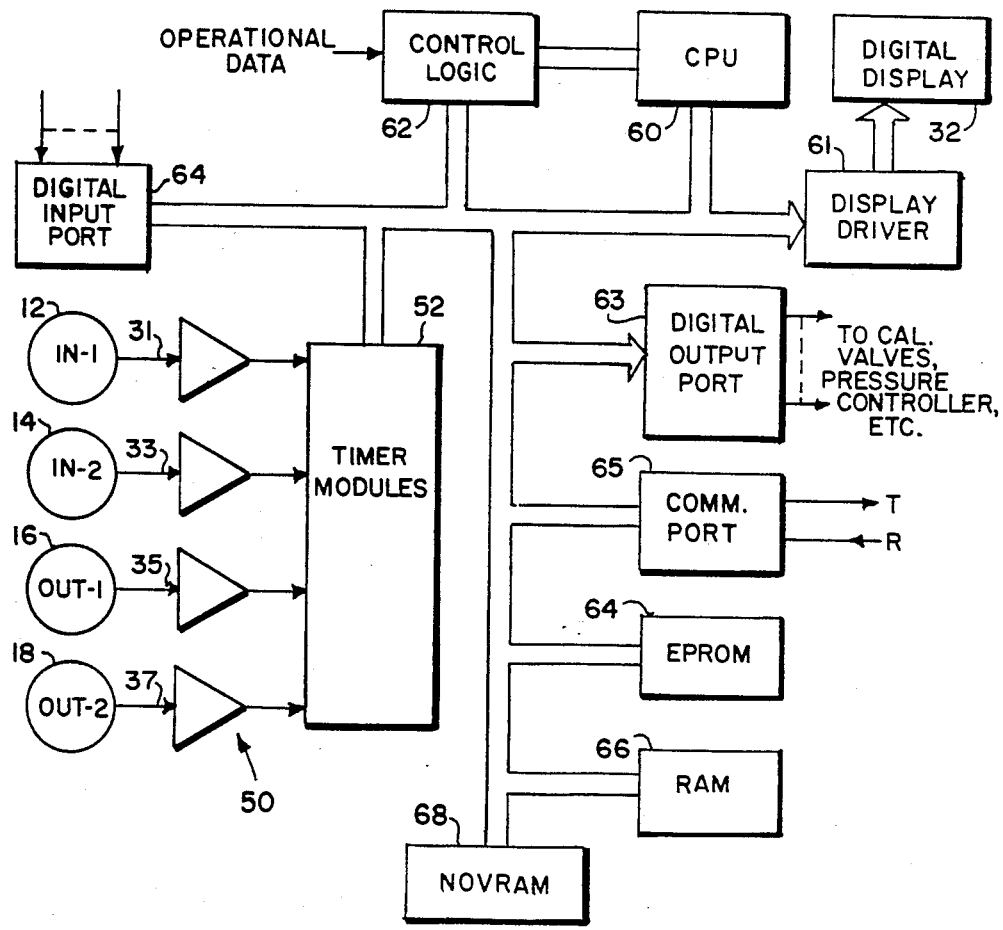
FIG. 2 is a block diagram of the computer system of the apparatus shown in FIG. 1.

Turning now to FIG. 2, a simplified block diagram of the digital computer and associated elements thereof is shown. CPU 60 is connected via the appropriate buses to EPROM 64, RAM 66, and NOVRAM 68. NOVRAM 68 is a non-volatile RAM having battery backup and stores temporary data which can survive power failure and will be available if required during subsequent use of the dialysis apparatus. Operational data is entered via digital input port 64 which includes all operator signals and status information from the various pumps and other operative elements of the hemodialysis equipment. Control logic 62 utilizes operational data from the arterial and venus pump being used during a treatment. Bearingless flow meters 12, 14, 16 and 18 are coupled via a set of signal processing amplifiers 50. Each of these amplifiers include a bandpass filter for the ac signal frequencies produced by the bearingless flow transducers over the flow rates for which the equipment is designed. Squaring amplifiers are also included in the signal processing amplifiers to produce clean signals for the computer. Timer modules 52 control the periods of taking samples from the flow transducers 12, 14, 16 and 18. A serial communication port 65 is provided to operate a printer or monitor and to receive input data. Digital output port 63 produces control signals for the bypass and calibration valves for the control of transmembrane pressure and other flow control functions. Display driver 61 operates digital display 32 to provide necessary information to the operator.

The algorithms for sequencing the computer through the various calibration steps are stored in programmable ROM 64.

As will now be recognized, a redundant flow measurement system has been provided for use in a hemodialysis apparatus in which the readings of a pair of input bearingless flow transducers can be monitored to ensure that both flow monitors are operational and in which a pair of output bearingless flow meters are monitored to ensure that the output flow measured by each is the same. The system frequency is directly proportional to the rate of rotation of the ring rotor 10 and therefore to the rate of flow of fluid through the flow meter.

Figure 3:
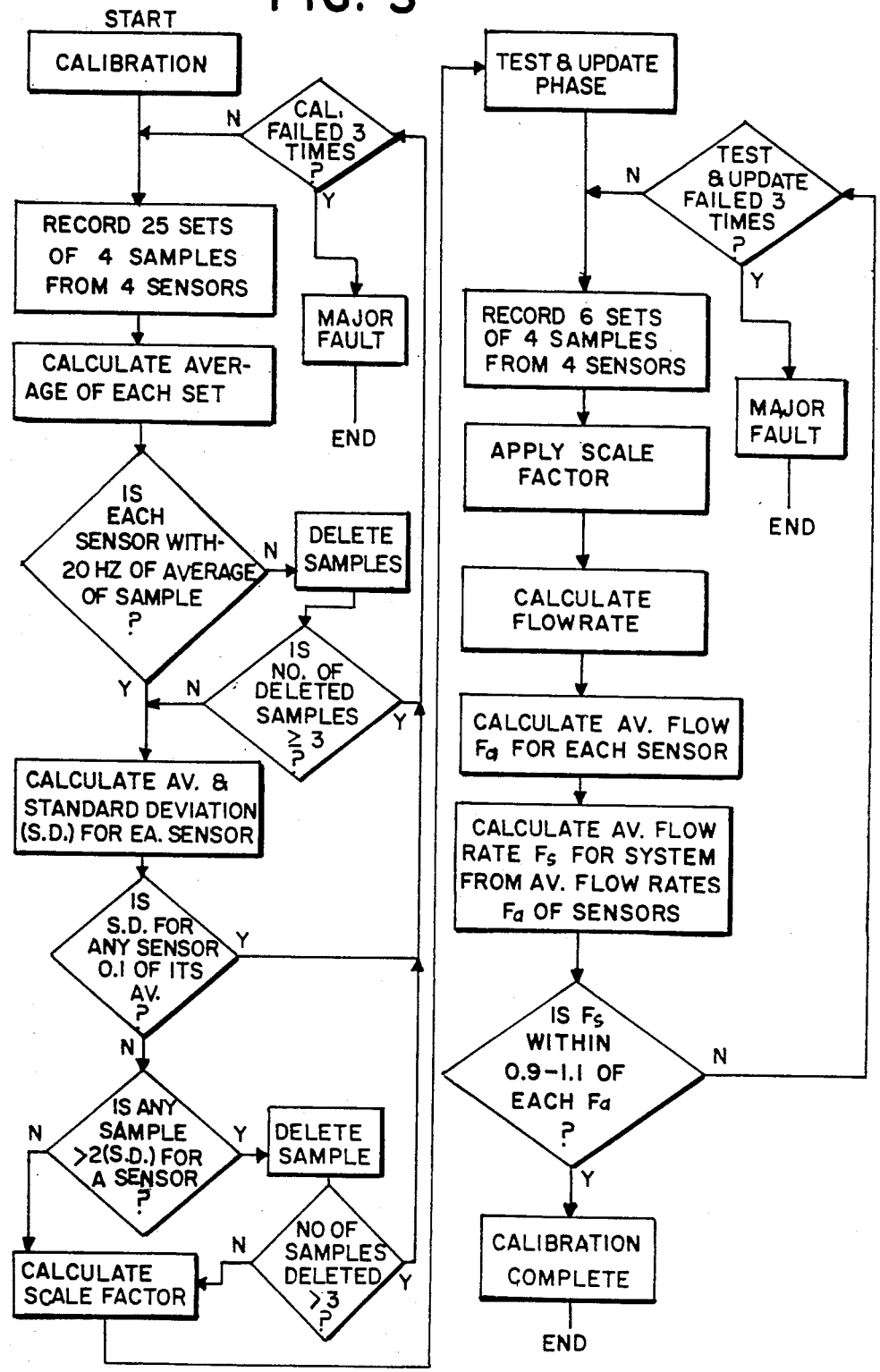
FIG. 3 is a flow diagram for the calibration algorithms of the system.

FIG. 3 is a flow diagram illustrating the algorithms stored in RAM 66 for performing the calibration functions. When calibration is initiated, bypass valve 20 is set to the bypass mode and calibration valve 24 is closed as previously explained, and a constant flow of dialysate through the flow transducers 12, 14, 16, and 18 is maintained throughout the calibration procedure.

The computer records a preselected number of sets of samples from the four transducers and calculates an average value of the frequency signal for each sample. For illustration, it is assumed that 25 sets will be recorded. A suitable tolerance, for example, 20 Hz, is applied and a determination made as to whether each sensor signal is within such tolerance with the sample average. Any sample failing this test is deleted. If 10% of the samples fail, the calibration procedure is restarted. If a third failure is noted, a major fault is indicated and calibration is terminated.

When the deviations of the samples from the average frequency are within tolerance, the average frequency for each sensor is calculated along with the standard deviation of the average for each sensor. If the standard deviation of any sensor is greater than 10% of its average, calibration is restarted. When this criterion is satisfied, the samples from each sensor are checked to see if any exceed twice the standard deviation of that sensor. If so, such samples are deleted. If the number of deleted samples exceeds 10% of the number of samples, calibration is restarted.

Next, a scale factor is calculated which, when applied to the readings of each transducer, will correct for variations in the transducers. To provide an additional check on the accuracy of the calibration, a test and update phase is preferably entered after the scale factor is determined.

In this procedure, a smaller number of samples is recorded from the four transducers; for example, 6 sets have been found to be satisfactory. The scale factor is applied to each sample and a flow rate calculated. The average flow rate $F_a$ for each sensor is then calculated as a system flow rate $F_s$ is determined from the four sensor average flow rates $F_a$.

The difference between the system average flow rate $F_s$ and each sensor average flow rate $F_a$ is noted and compared to a preselected tolerance. For example, it may be required that $F_s$ be within $+10\%$ of each $F_a$ value. If the tolerance is not met, the test and update is repeated. Failure to pass three times is considered a major fault, and the operation is terminated for repairs.

An improved flow measurement system applicable to a use requiring high accuracy has been described with reference to hemodialysis equipment. However, it will be recognized by those of skill in the art that the system may be used in any process requiring accurate flow measurement and continuous monitoring of such measurements for false flow readings and faults in the measurements. Although specific hardware and software configurations have been disclosed for exemplary purposes, various changes can be made to such configurations without departing from the spirit and scope of the invention.

We claim:

1. In a flow rate measurement and monitoring system having flow rate transducers, said transducers having inherent inaccuracies, said system having a calibration phase and an operational phase, the improvement comprising:

a first flow rate transducer for producing a first electrical signal proportional within a first inherent error to a rate of flow of a fluid therethrough;

a second flow rate transducer connected in tandem with said first flow rate transducer for producing a second electrical signal proportional within a second inherent error to said rate of flow of said fluid therethrough;

a computer connected to said first and second flow rate transducers for receiving said first and second electrical signals;

program means resident in said computer, said program means including a calibration algorithm for calculating, during said calibration phase of operation of said system, a difference between said first and second signals due to said first and second inherent errors, and to calculate a scale factor and an average of said first and second electrical signals;

said program means thereafter applying said scale factor to said first and second signals during said operational phase of said system; and said program means including a monitoring algorithm for monitoring said difference and for indicating a fault, during said operational phase of said system, when said difference between said first and second electrical signals changes.

2. In a system having first flow rate transducers for measuring a rate of flow of a first fluid in a first part of said system and having second flow rate transducers for measuring a rate of flow of a second fluid flow combined with said first fluid flow in a second part of said system, a subsystem for measuring said rate of flow of said second fluid from a rate of flow measurement of said first fluid prior to such combination of said fluid flows and a rate of flow measurement of said first fluid in combination with said second fluid, said system having a calibration period and an operational period, comprising:

a first flow rate transducer, having an inherent inaccuracy, for producing a first electrical signal proportional within a first inherent error to a rate of flow of said first fluid therethrough;

a second flow rate transducer, having an inherent inaccuracy, connected in series with said first flow rate transducer for producing a second electrical signal proportional within a second inherent error to said rate of flow of said first fluid therethrough;

a third flow rate transducer, having an inherent inaccuracy, connected to receive said combined flow of said first and second fluids for producing a third electrical signal proportional within a third inherent error to a rate of flow of said combined flow of said first and second fluids;

a fourth flow rate transducer, having an inherent inaccuracy, connected in series with said third transducer for producing a fourth electrical signal proportional within a fourth inherent error to said rate of flow of said combined flow of said first and second fluids;

means for temporarily causing said first fluid only to flow through said third and fourth transducers during said calibration period of said system and for causing said combined fluids to flow through said third and fourth transducers during said operational period of said system;

a computer connected to said first, second, third, and fourth flow rate transducers for receiving said first, second, third, and fourth electrical signals;

program means resident in said computer, said program means including a calibration algorithm for calculating first scale factors from a difference between said signals from said first, and second transducers during said calibration period of said system, said first scale factors applied to said first and second signals during said operational period of said system for correcting for the difference therebetween, said calibration algorithm for calculating second scale factors from a difference between said signals from said third and fourth transducers during said calibration period of said system, said second scale factors applied to said third and fourth signals during said operational period of said system for correcting for the difference therebetween; and said program means including a monitoring algorithm for monitoring said difference between said first and second electrical signals, and said difference between said third and fourth electrical signals during said operational period and for indicating a fault when at least one of said differences varies from the corresponding difference measured during said calibration period.

3. The system as recited in claim 2 in which said calibration algorithm includes means for indicating a fault when any of said differences exceeds a preselected amount.

4. The system as recited in claim 2 in which said calibration algorithm defines a calibration phase, and a test and update phase.

5. The system as recited in claim 4 in which said calibration algorithm produces a set of plurality of samples of values of said electrical signals and calculates an average value for each set and a standard deviation for each set.

6. The system as recited in claim 5 in which said calibration algorithm includes means for indicating a fault when the standard deviation of a set of signals from any one of said transducers exceeds a preselected percentage of said average value of said set.

7. A method of monitoring and calibrating a pair of tandem connected electrical transducers for measuring a rate of flow of a fluid through a system, the pair of transducers connected to a computer, the computer for receiving electrical signals from the transducers essentially proportional to the rate of flow of the fluid therethrough, comprising the steps of:

(a) producing a constant rate of flow of the fluid through each of the pair of transducers;

(b) initiating a calibration phase of the system;

(c) recording a set of samples of the fluid flow rate signals in the computer;

(d) calculating an average fluid flow rate signal level from each set of samples;

(e) comparing an average of each of the set of samples and calculating a scale factor to produce equal flow measurement values from each transducer;

(f) initiating an operational phase of the system;

(g) comparing calculated flow measurement values from each transducer during the operational phase; and (h) initiating a fault indication when such compared calculated values differ from each other by a preselected percentage.

* * * * *